US011434121B1

(12) United States Patent
Lindquist et al.

(10) Patent No.: US 11,434,121 B1
(45) Date of Patent: Sep. 6, 2022

(54) ENVIRONMENTAL ALERT SYSTEM FOR AERIAL DEVICE

(71) Applicant: Altec Industries, Inc., Birmingham, AL (US)

(72) Inventors: David Lindquist, Cameron, MO (US); William Naber, Saint Joseph, MO (US)

(73) Assignee: Altec Industries, Inc., Birmingham, AL (US)

( * ) Notice: Subject to any disclaimer, the term of this patent is extended or adjusted under 35 U.S.C. 154(b) by 0 days.

(21) Appl. No.: 17/560,539

(22) Filed: Dec. 23, 2021

(51) Int. Cl.
*H02J 3/36* (2006.01)
*B66F 17/00* (2006.01)
*G01N 33/00* (2006.01)
*G08B 21/18* (2006.01)

(52) U.S. Cl.
CPC ....... *B66F 17/006* (2013.01); *G01N 33/0063* (2013.01); *G08B 21/182* (2013.01)

(58) Field of Classification Search
CPC .. B66F 17/006; G01N 33/0063; G08B 21/182
See application file for complete search history.

(56) References Cited

U.S. PATENT DOCUMENTS

| 4,114,088 A | 9/1978 | Laws |
| 4,877,422 A | 10/1989 | Walbridge et al. |
| 2018/0159331 A1* | 6/2018 | Bilic .................. H02J 3/36 |

FOREIGN PATENT DOCUMENTS

CN          209119788      *   8/2018

* cited by examiner

*Primary Examiner* — Hongmin Fan
(74) *Attorney, Agent, or Firm* — Erise IP, P.A.

(57) ABSTRACT

An environmental alert system and method for an aerial device including a boom having both insulative and conductive members is disclosed. Temperature, moisture, and humidity sensors are employed on both sides of a location that the boom transitions from being constructed of metal to a dielectric. If environmental data is received indicating the possibility of breakdown in dielectric integrity of the insulative portion due to environmental conditions, warnings are issued to operators.

20 Claims, 6 Drawing Sheets

ENVIRONMENTAL ALERT SYSTEM FOR AERIAL DEVICE

BACKGROUND

1. Field

Embodiments of the invention relate to alert systems for environmental conditions. More specifically, embodiments of the invention relate to systems for the detection of breakdowns in dielectric integrity due to humidity or condensation in the surrounding environment of an aerial system.

2. Related Art

Aerial devices are commonly used to perform tasks at heights not typically or reasonably reached by other means. For example, aerial devices can be used to hoist workers up to perform tasks such as trimming trees, building construction, roofing, sign maintenance, electrical line maintenance and erection, etc. At times, these aerial devices may need to work in inclement weather.

A typical aerial device is largely made of conductive materials. But portions of the boom of an aerial device have been constructed of low-conductivity materials, e.g., fiberglass, so that if another portion of the boom comes into contact with a power line or other source of high voltage, electricity will be prevented from traveling through the aerial device. To prevent this, a dielectric gap has been formed across the boom of some aerial devices by incorporating nonconductive materials into portions of the system.

The environment in which an aerial device is operating can change quickly. This can cause a break down in the dielectric integrity of the insulating portion of the boom. Environmental conditions that may lead to dielectric breakdown include condensation, or the formation of moisture precipitating out of the air. Those skilled in the art will recognize that condensation or precipitation onto the insulative portion of boom have the potential of creating a dielectric breakdown.

SUMMARY

In some embodiments, an aerial device includes a boom that is configured to be operatively attached to a base. The boom extends up and supports a platform in a plurality of positions in embodiments. In some embodiments, the boom has conductive and insulative portions. One or more environmental sensors can be located on either the conductive portion of the boom, the insulative portion of the boom, or both. A computing system is operatively connected to the environmental sensors. In embodiments, the computer includes a processor that is configured to receive a reading from the environmental sensors and transmit an alert to a user of the aerial device of a detected environmental condition indicative of a breakdown in dielectric integrity of the insulative portion of the boom.

In another embodiment, an environmental alert system includes: a computing system operatively connected to a group of environmental sensors located on an insulative portion of a boom of an aerial device, where the group of environmental sensors includes a temperature sensor and either a humidity sensor or a moisture sensor. The computing system is configured to evaluate a plurality of readings from the group of environmental sensors and determine whether an environmental condition exists that is indicative of a dielectric breakdown in the insulative portion, and is also configured to transmit a warning to an operator of the aerial device, the warning indicating the existence of the environmental condition.

In some embodiments, an environmental alert system includes: a processor and one or more non-transitory computer readable storage media having a computer program stored thereon for alerting one or more users of an aerial device, wherein the computer program instructs the processor to perform actions, including initiating the program upon receiving an indication that a boom has been activated; monitoring environmental conditions using at least one environmental sensor; detecting the values for one or more environmental conditions using the at least one environmental sensor; using the values to determine if the values indicate a risk of dielectric breakdown of a boom component; and transmitting an alert to a user if the values are determined to indicate a risk of dielectric breakdown.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the invention will be apparent from the following detailed description of the embodiments and the accompanying drawing figures.

BRIEF DESCRIPTION OF THE DRAWING FIGURES

Embodiments of the invention are described in detail below with reference to the attached drawing figures, wherein.

The drawing figures do not limit the invention to the specific embodiments disclosed and described herein. The drawings are not necessarily to scale, emphasis instead being placed upon clearly illustrating the principles of the invention.

DETAILED DESCRIPTION

The following detailed description references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the invention. The following detailed description is, therefore, not to be taken in a limiting sense. The scope of the invention is defined only by the appended claims, along with the full scope of equivalents to which such claims are entitled.

In this description, references to "one embodiment," "an embodiment," or "embodiments" mean that the feature or features being referred to are included in at least one embodiment of the technology. Separate references to "one embodiment," "an embodiment," or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the technology can include a variety of combinations and/or integrations of the embodiments described herein.

Figure 1A:
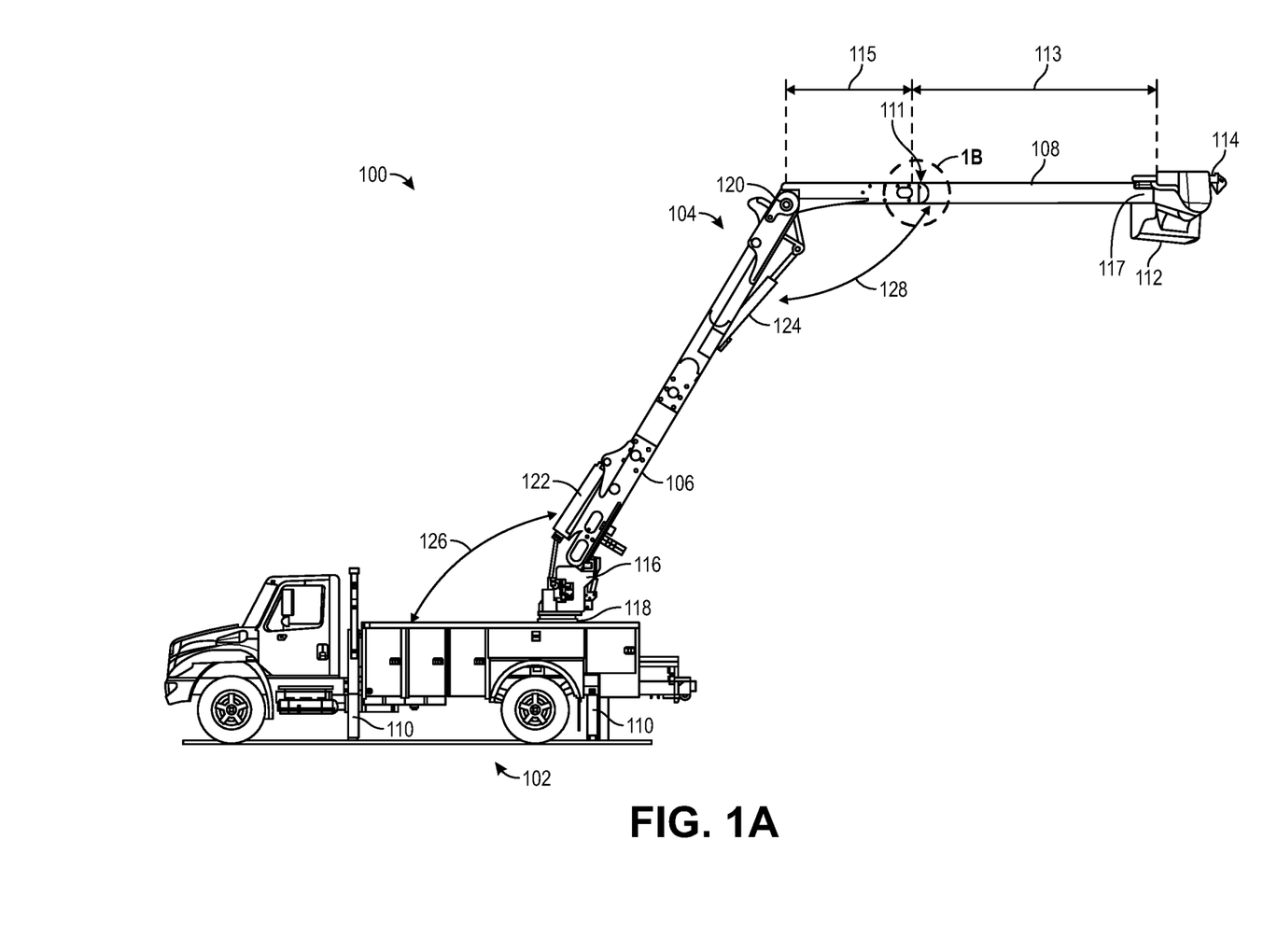
FIG. 1A is a side view of an aerial device into which the systems and methods disclosed herein might be incorporated in some embodiments.

FIG. 1 shows a side view of an aerial device 100 into which the environmental dielectric alert system might be incorporated in embodiments. Similar components illustrated in different figures are enumerated with like numerals and may include alternative embodiments.

The aerial device 100 may include some sort of base that supports an extendable member configured for reaching (e.g., a boom 104). In the embodiment depicted in FIG. 1, the base 102 is a utility truck. In some embodiments, the base 102 may be a crane, a derrick digger, or any other base including an extendable member. In some embodiments, the boom 104 provides an extendable member for moving a platform 112. In some embodiments, the boom 104 may include a lower boom 106 and an upper boom 108. The base 102 provides a stable support, which may include outriggers 110, for supporting a load applied to the boom 104 and/or the platform 112. In an embodiment, the platform 112 includes a jib 114 configured for securing objects thereto. In some embodiments, the platform 112 may rotate to alter its orientation with respect to the boom 104. The boom 104 may fold into a collapsed position, which enables transporting via a mobile version of the base 102.

The boom 104 is mechanically coupled to, and configured to support, the platform 112. The optional platform 112 may be located at the distal end (with respect to the mobile base 102) of the upper boom 108. The upper boom 108 may include an optional telescoping arm (not shown) that extends from, and retracts within, the upper boom 108. The lower boom 106 may be mechanically coupled to a turntable 116 configured for rotating the boom 104. A pedestal 118 may be included to support the turntable 116 and is mechanically coupled to the base 102.

In operation, the platform 112 is raised by a combination of the lower boom 106 pivoting upwards, the upper boom 108 pivoting about an elbow 120, and the telescoping arm optionally extending out of the upper boom 108.

In an embodiment, the platform 112 is configured for hoisting a user into the air to, for example, work on a powerline or any other elevated thing. Prior to extending the boom 104, the base 102 may be moved to an appropriate location and stabilized. The boom 104 may be rotated about the turntable 116, and extended upwards and outwards away from the base 102 by pivoting the lower boom 106, the upper boom 108, and by extending the telescoping arm. Various combinations of these movements may be employed to position the platform 112 around base 102. In some embodiments, movement of the platform 112 may be operated by a user located on the platform 112. In some embodiments, operation of the platform 112 may be controlled by an operator not located on platform 112 (e.g., on the ground). In both cases, the user may not be able to see all aspects of the moving portions of the boom 104 (e.g., an elevator 130, lower boom 106, upper boom 108, elbow 120, etc.). Accordingly, certain components may, unbeknownst to the user, come within a dangerous proximity to a voltage or current source (e.g., a high-voltage powerline, a telecommunications line, etc.). As will be discussed further below, the environmental dielectric alert system 300 may, in some embodiments, be configured to warn a user or operator that there is a risk of a dielectric breakdown due to environmental conditions, such as humidity.

Figure 1B:
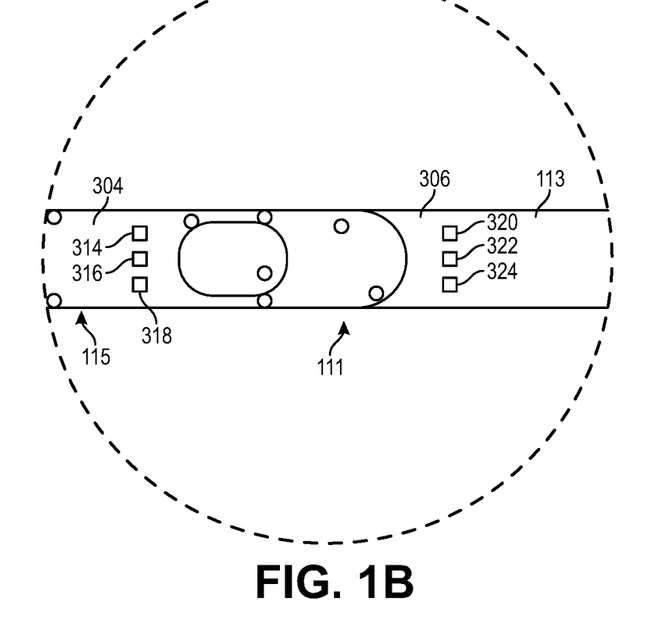
FIG. 1B is a magnified view highlighting the area identified in FIG. 1A.

Specific to these concerns, in certain embodiments, the upper boom 108 and any telescoping arm that may extend from upper boom 108 may be at risk of sparkover when work is being done proximate a high voltage source. The upper boom 108, in the disclosed embodiment, includes a conductive portion 115 and a nonconductive insulative portion 113, defining a conductive/insulative interface 111 therebetween where the boom transitions from the conductive material to the dielectric or nonconductive material. In some embodiments, the conductive material may be a metal. Any telescoping arm that may extend from the upper boom 108, in embodiments might also be made of an electrically insulating material defining an insulative portion of the overall aerial device to further insulate between the base 102 and the bucket 112 in the case of a high-voltage exposure.

In some embodiments, a dielectric composite material (e.g., fiberglass) can be utilized to construct the insulative portion 113 as well as any extending apparatus from the upper boom 108. The insulative portion 113 enables safe operation near electrical hazards (e.g., power lines). Such an insulating composition may, in embodiments, be configured to protect a user within platform 112 or an operator near base 102 from a situation where in which a portion of boom 104 comes in contact or close proximity with a portion of a high voltage system. Such an insulating gap may require the use of electrically insulating signaling methods between base 102 and platform 112, such as the use of fiber optic cables or wireless technologies instead of conductive circuitry, such as including metal or a direct wired connection.

Aerial device 100 may include a first boom hydraulic cylinder 122 and a second boom hydraulic cylinder 124 configured to move certain components of boom 104. For example, first boom hydraulic cylinder 122 may be configured to move lower boom 106 around lower boom joint angle 126. In some embodiments, second boom hydraulic cylinder 124 may be configured to move upper boom 108 around upper boom joint angle 128.

Figure 2:
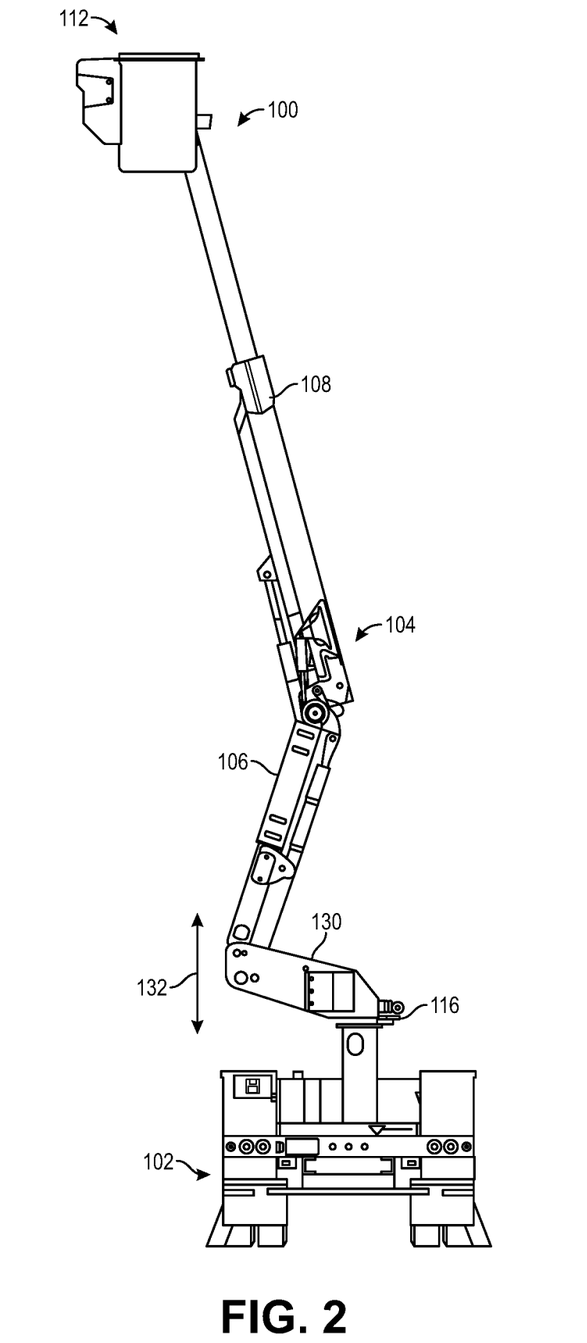
FIG. 2 is a rear view of an aerial device of FIG. 1.

As depicted in FIG. 2, in some embodiments, aerial device 100 may include a turntable 130. In some embodiments, turntable 130 may be disposed between base 102 and lower boom 106. In some embodiments, turntable 130 may be configured to raise or lower boom 106 in a substantially vertical direction (e.g., direction 132).

Boom 104 may be rotatable and extendable. For extending its reach, in some embodiments the boom 104 may comprise a multi-segment boom having more than one segment. For example, as depicted in FIGS. 1-2, the boom 104 may include at least lower boom 106 and upper boom 108. The boom segments may be mechanically coupled in a variety of ways to enable various movements including but not limited to extending, contracting, raising, lowering, and rotating. For example, some boom segments may be pivotally coupled with joints for articulating, while other boom segments may be telescoping for extending/contracting. However, as mentioned, the boom 104 may include greater than two segments without departing from the scope hereof, such as elevator 130. Movement of the boom 104 may be by one or more hydraulic cylinders (e.g., first boom hydraulic cylinder 122, second boom hydraulic cylinder 124, etc.) mechanically coupled to segments of the boom 104, among other mechanical devices (e.g., cables).

A base 102 is provided to mechanically support the boom 104. The base 102 may be stationary (e.g., a fixed structure such as a crane or an oilrig) or mobile (e.g., an earth-working machine or a utility truck). In certain embodiments, the lower boom 106 may be mechanically coupled to the base 102, and the upper boom 108 may be mechanically coupled to the lower boom 106 via elbow 120 (see e.g., FIGS. 1-2).

An optional platform 112 may be mechanically coupled to a tip of the boom 104 at its distal end. In some embodiments, the base 102 may be mechanically coupled to a first end of the boom 104 (e.g., the proximal end), and the optional platform 112 may be mechanically coupled to a second end of the boom 104 (e.g., the distal end), opposite the first end. In some embodiments, the platform 112 may be configured to support one or more operators (e.g., in a utility bucket).

Despite the protection offered by insulating a portion of the boom, there is always a risk that the integrity of the dielectric properties of that portion can be lowered by environmental conditions. Therefore, an alert system is disclosed for the purpose of providing an additional layer of protection.

Figure 3:
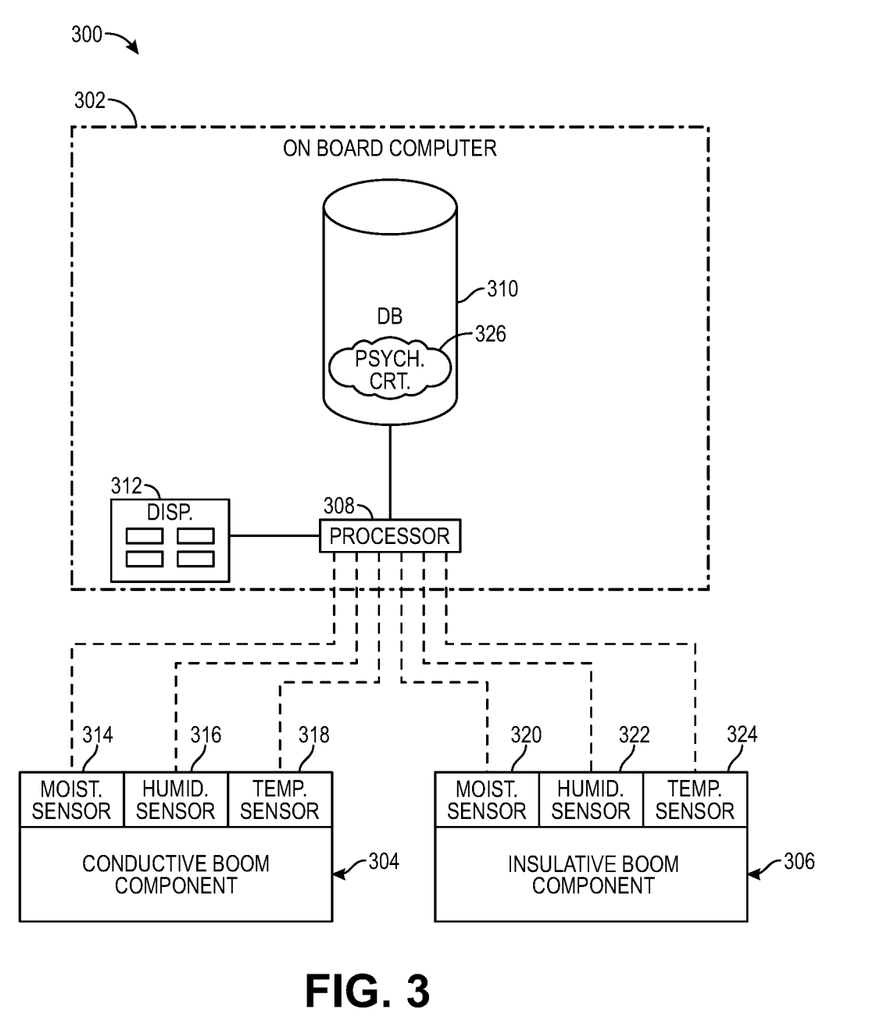
FIG. 3 illustrates a block diagram of an exemplary environmental dielectric alert system, in some embodiments.

FIG. 3 shows a block diagram representing an exemplary environmental dielectric alert system 300. The alert system 300 can, in some embodiments, be utilized on an aerial device, e.g., aerial device 100, and be controlled by a computer system 302.

In embodiments, the computer system 302 might comprise a computer, microcontroller, microprocessor, or programmable logic controller (PLC). In terms of location, the computer system 302 might be located in a variety of, or multiple locations places on the aerial device 100. In some embodiments, the computer system 302 might include a computer located on (or in) the base 102 of aerial device 100. In some embodiments, the computer system 302 may comprise a computing device disposed on the turntable 116 of aerial device 100. In some embodiments, the computer system 302 may include a computer disposed on the boom 104 of aerial device 100. In some embodiments, the computer system 302 may include a computer disposed on the platform 112 of aerial device 100 or on a mobile device. In some embodiments, computer system 302 may comprise more than one computing device located in any of the already described or other locations on aerial device 100. In these embodiments, the more than one computing device may be operatively connected for communication therebetween.

In embodiments, the computer system 302 is centered around at least one processing component 308. The processing component 308 accesses data existing on a database 310, and can receive and display data via a user interface 312. In some embodiments, database 310 includes non-transitory computer readable storage media having computer programs stored thereon. In some embodiments, the user interface might include physical buttons, levers, a computer keyboard, an interactive touch screen, a hand-held control stick (e.g., a joystick or sidestick controller), or a mobile device. The interface might also comprise numerous interfaces operating together with a common or multiple separate computing devices.

The interface 312 is used to interface with the processing component 308 and cause it to operate using programming existing on the database 310. That same interface, or an additional optional interface can enable an operator to acknowledge a warning or alert, and take corrective action.

The environmental alert system 300 may provide an alert that informs an operator of the aerial device 100 of a potential unsafe situation, such as high humidity, condensation, or precipitation on or about the insulating components of the aerial device. The system 300 might also include one or more alert devices to produce the alert such as alarms, lights, display devices, speaker systems, buzzers, color-coded illuminations (e.g., flashing yellow/red), or other similar alerting indications. These alert indicators can be located at any location on the aerial device 100, e.g., on the boom, in or on the base, at the bucket, etc.

The computing system 302, in some embodiments, receives information regarding environmental conditions (e.g., temperature, humidity, the existence of moisture, etc.) at a location on an insulating component surface 306 on the insulative portion 113 of the upper boom 108. The system, in some embodiments, receives environmental information from a relatively conductive component surface 304 on the conductive portion 115 of the upper boom 108.

In some embodiments, the locations of the component surfaces 306 and 304 exist on opposite sides of the interface 111 between the insulative and conductive portions 113 and 115 (see FIGS. 1A and 1B). In other embodiments, the sensors are located at different locations on the insulative and conductive portions 113 and 115 not at the interface. Therefore, the locations of these sensor groups on each portion should not be limited to any particular location unless otherwise specified in the claims.

In some embodiments, the conductive component surface location 304 includes one or more environmental sensors. As shown in FIG. 3, the one or more environmental sensors might include any of a moisture sensor 314, a humidity sensor 316, and a temperature sensor 318, each of which can be mounted onto a surface location 304 on the conductive portion 115.

Similarly, in some embodiments, the insulating component surface location 306 also includes at least one environmental sensor. Here the at least one environmental sensor might include any of (again, referring to FIG. 3) a moisture sensor 320, a humidity sensor 322, and a temperature sensor 324, each of which can be mounted on a surface location 306 of the insulative portion 113. The existence of these sensors will be utilized by the computer system 302 to evaluate the environmental conditions at each surface location.

Because sensors 320, 322, and 324 are located on an insulative component 113, they can be connected by a non-conductive fiberoptic arrangement, wireless enabled or otherwise communicate with the computer system 302 to avoid the necessity of conductive wiring, which would lower the dielectric integrity of the insulative portion 113. Sensors 314, 316, and 318 on the conductive portion 115 could be either wired or wireless.

The sensor group on the conductive portion 115 (sensors 314, 316, and 318) can be used to create redundancy and check for accuracy in readings detected for the group of sensors on the insulative portion 113 (sensors 320, 322, and 324), and vice versa depending on the way the sensors are being utilized at a particular time.

Optionally, an additional set of environmental sensors (not shown) might be located on a non-conductive surface at or near a distal end location 117 of the aerial device 100 for the purpose of providing additional redundancy or values which can be used. This arrangement also could include one, two, or all of a moisture, humidity, and/or temperature sensor. These redundant sensors at distal end location 117 could also be connected via a fiberoptic connection wirelessly enabled, since any conductive electrical conduits might otherwise appreciably lower the dielectric properties of the insulative portions of the boom. Additionally, it is contemplated that these redundant sensors could be "read" by an additional microprocessor (or similar) at the distal end 117 and the values be transmitted via fiberoptics, wireless, etc. to the appropriate system computer (at any location).

Figure 4:
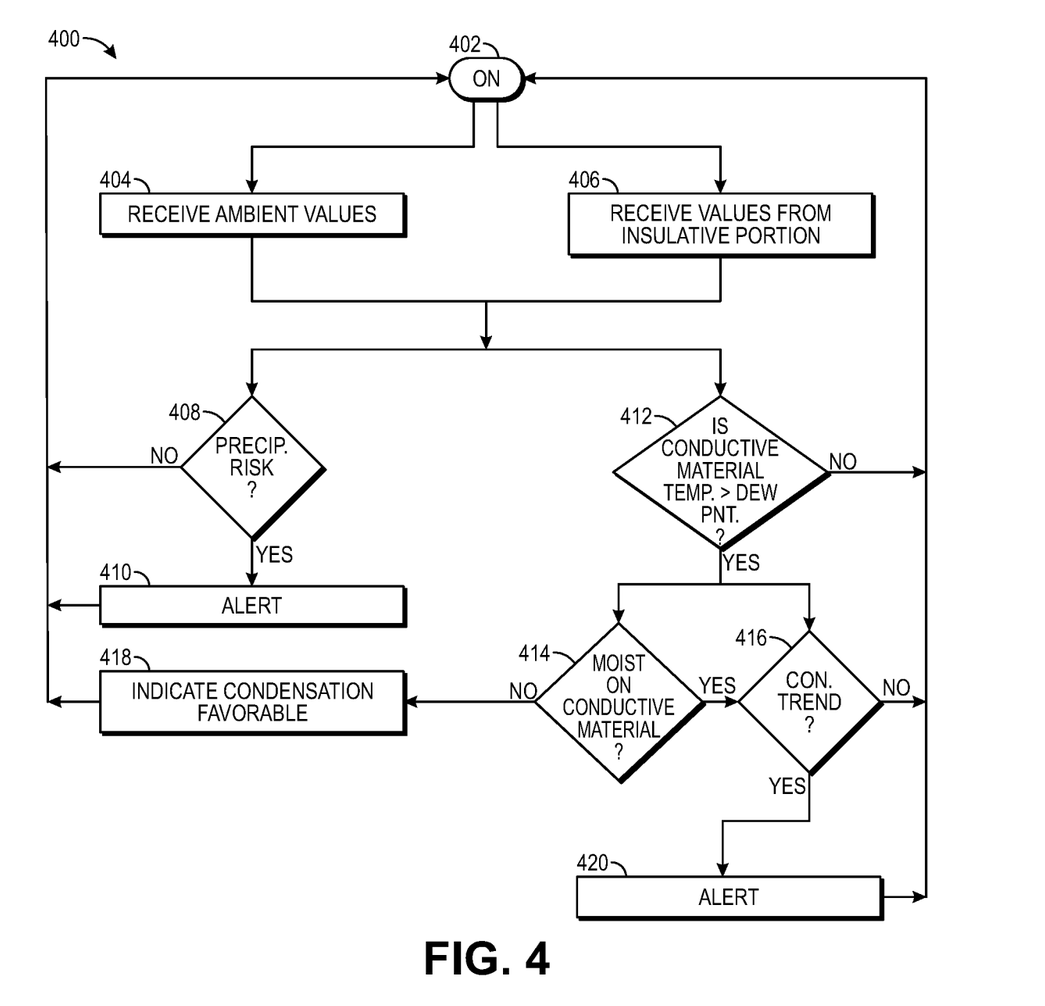
FIG. 4 is a process flow diagram reflecting an embodiment of a process executable along with the system embodiment shown in FIG. 3.

The process flow FIG. 4 shows an embodiment for an alert process 400 configured to operate on the processing component 308 to warn a user that environmental conditions exist that might appreciably lower the dielectric properties of the insulative portion 113 of the upper boom 108.

As a preliminary step (not shown in FIG. 4), sensors are placed or mounted on the aerial device (either permanently or temporarily). The sensors can be optionally mounted on surface locations 304 and 306 (see FIG. 3) existing on opposite sides of the interface 111 (see FIGS. 1A and 1B) between the insulative and conductive portions 113 and 115. Additionally, sensors can optionally be located at the distal end 117 of the boom. The sensors (which might be independent sensor devices, or aggregated sensor systems) can be configured to communicate with the computer system 302.

In a step 402, the environmental alert process is initiated. In an embodiment, the process is initiated upon detection of a Power Take-Off (PTO) signal, which in some aerial devices is a detection of power being diverted to boom operation. This ensures that when the boom is in operation, the environmental alert process is executing.

Next steps 404 and 406 are shown in FIG. 4 as being executed in parallel, but could alternatively be executed in series. In step 404, the processing component 308 of the computer system 302 receives ambient values from one or more of sensors 314, 316, and 318 located on the conductive component surface 304. In a step 406, the computer system 302 receives readings from one or more of sensors 320, 322, and 324 located on the insulative portion 113. After reading these values, the process executes several analytical queries used to determine the need for warnings, alerts, and notifications in the following steps.

After the readings have been taken in tandem steps 404 and 406, the process moves on to two different query steps. Of these, in a query step 408, a decision is made as to whether the current environmental conditions on the insulative portion 113 reflect a precipitation risk. To do this, the process accesses the readings from one or more of (i) the humidity sensor 322, and (ii) the temperature sensor 324. The values obtained can be used to determine whether conditions are suitable for moisture to precipitate out of the air. Temperature sensors may sense the ambient temperature and/or the temperature of the insulative component surface 306. Those skilled in the art will recognize that precipitation is a function of humidity and temperature. This can be seen looking at the psychrometric chart 500 of FIG. 5 which shows temperature along an X-axis 502 and humidity along a Y-axis 504 of the chart 500. The chart shows a saturation temperature curve 506 which represents a level at which precipitation begins based on particular temperature and humidity values. Values falling above the saturation temperature curve 506 will result in precipitation, and values below the saturation temperature curve 506 will not result in precipitation.

Figure 5:
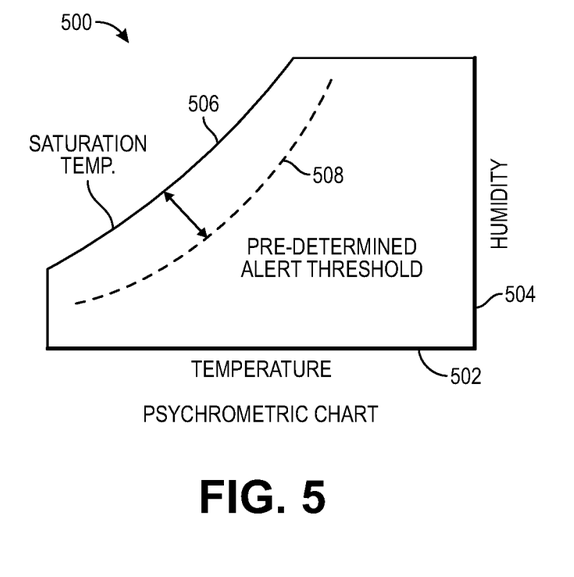
FIG. 5 is a psychrometric chart utilized in establishing a pre-determined alert threshold for embodiments of the process of FIG. 4.

Because users of the aerial device will need time to take corrective action to avoid operating in dangerous environmental conditions, e.g., lower the boom away from electrical hazards before precipitation starts, a pre-determined alert threshold curve 508 has been established in some embodiments. In some embodiments, a psychrometric chart 326, and the pre-determined alert threshold curve 508 can be electronically stored in database 310. See FIG. 3. Those skilled in the art will recognize that the processor 308, based on programming contained in database 310, can apply temperature and humidity values received from one or more of sensors 324 and 322 on the insulating component surface 306, and use either electronic tables or a set formula to determine whether a resulting X-Y value falls above or below the saturation temperature curve 506. Additionally, the processor could be looking for values that fall above or below the pre-determined alert threshold 508. In such an instance, electronic tables or a set formula to determine whether a resulting X-Y value falls above or below the saturation temperature curve 506 and/or pre-determined alert threshold 508. If, in step 408 the value is above the saturation temperature curve 506, the process moves on to a step 410 where an alert is transmitted to alert a worker that an environmental condition exists using any of the alert devices located in any of the possible locations mentioned above. In some embodiments, the alert appears on the display 312 and includes information descriptive of possible precipitation. After the alert is transmitted in step 410, or if there is no precipitation risk detected in step 408, the process loops back up to start 402 to continue monitoring. Monitoring may be done continuously or at set intervals as specified by a user or by computer system 302.

A query step 412 follows receiving steps 404 and 406 on the other side of the parallel process. There, a determination is made as to whether the current temperature reading from the temperature sensor 318 on the conductive component surface 304 is greater than the dew point temperature (the value for which is saved in the database 310) or a predetermined offset dew point threshold. In step 412, if the temperature reading is below the dew point (or the predetermined offset), the process loops back up to start 402 to continue monitoring. If, in step 412, the temperature value measured is above the dew point, the process moves on to two parallel query steps 414 and 416. Temperature sensors may sense the ambient temperature and/or the temperature of the conductive component surface 304.

In step 414, a determination is made as to whether moisture is detected on the conductive portion 115 at location 304. This is done using the readings received from the moisture sensor 314 on the conductive portion 115. If moisture is not detected, a message (e.g., a warning) is transmitted in a step 418 to the effect that condensation is favorable, and then the process loops back up to start 402 to continue monitoring.

If, however, moisture is detected in step 414, the process converges on query step 416 where a determination is made as to whether there is a trend towards condensation. In order to recognize such a trend, the computing system 302 can be configured to continually save moisture, humidity, and temperature values from some or all of the sensors (e.g., sensors 314, 316, 318, 320, 322, and 324). These saved values can be compared against newly received data received from the sensors 314, 316, or 318 on the insulating component surface 306 towards the development of condensation on the nonconductive component. If a trend towards condensation is detected, an alert is transmitted to the operator in a step 420 that action is required due to the condensation risk. Additionally, the processing component could look for a psychrometric trend that would validate that the moisture detected by moisture sensor 314 and alerted by process step 414 is environmental and not some residual moisture detected by moisture sensor 314 from some other source that is not likely to reduce the dielectric integrity of the aerial insulating portion, to prevent a false positive alert.

Although the invention has been described with reference to the embodiments illustrated in the attached drawing figures, it is noted that equivalents may be employed and substitutions made herein without departing from the scope of the invention as recited in the claims.

Having thus described various embodiments of the invention, what is claimed as new and desired to be protected by Letters Patent includes the following:

1. An aerial device, comprising:
a boom configured to be attached to a base and configured to extend upward and support a platform in a plurality of positions,
said boom comprising a conductive portion and an insulative portion;
a plurality of environmental sensors located on either the conductive portion of the boom or the insulative portion of the boom;
a computing system operatively connected to one or more environmental sensors;
said computing system comprising a processor, the processor configured to receive a reading from the one or more environmental sensors and transmit an alert to a user of the aerial device,
said alert indicating a detected environmental condition indicative of a breakdown in dielectric integrity of the insulative portion of the boom,
a first environmental sensor in the plurality of environmental sensors being located on the conductive portion of the boom, and a second environmental sensor in the plurality of environmental sensors being located on the insulative portion of the boom.

2. The aerial device of claim 1, wherein the one or more environmental sensors comprises a temperature sensor.

3. The aerial device of claim 1, wherein the one or more environmental sensors comprises a moisture sensor.

4. The aerial device of claim 1, wherein the one or more environmental sensors comprises a humidity sensor.

5. The aerial device of claim 1, wherein the one or more environmental sensors comprises at least two different sensors selected from the group consisting of a humidity sensor, a moisture sensor, and a temperature sensor.

6. The aerial device of claim 1, wherein the one or more environmental sensors includes at least two different kinds of sensors.

7. The aerial device of claim 1, wherein the processor is configured to:
determine a precipitation risk upon receiving a humidity value from a humidity sensor and a temperature value from a temperature sensor; and
then transmit the alert if the humidity versus temperature values exceed a predetermined threshold.

8. The aerial device of claim 1, wherein the processor is configured to indicate condensation is favorable if:
a temperature reading from a temperature sensor on the conductive portion of the boom is above a dew point temperature.

9. The aerial device of claim 1, wherein the processor is configured to record values received from the one or more environmental sensors and transmit the alert based on a trend indicative of a breakdown in dielectric integrity of the insulative portion of the boom.

10. An environmental alert system comprising:
a first group of environmental sensors located on an insulative portion of a boom of an aerial device, the first group of environmental sensors comprising a temperature sensor and either a humidity sensor or a moisture sensor; and
a second group of environmental sensors located on a conductive portion of the boom;
a computing system operatively connected to the first group of environmental sensors, the computing system configured to evaluate a plurality of readings from the first group of environmental sensors and determine whether an environmental condition exists which is indicative of a dielectric breakdown in the insulative portion;
the computing system additionally being configured to transmit a warning to an operator of the aerial device, the warning indicating the existence of the environmental condition.

11. The environmental alert system of claim 10, wherein the first group of environmental sensors on the insulative portion of the boom are located proximate the second group of environmental sensors on the conductive portion of the boom across a transition between the insulative portion and the conductive portion.

12. The environmental alert system of claim 10, wherein the first group of environmental sensors includes the humidity sensor, and a temperature reading from the temperature sensor and a humidity reading from the humidity sensor are used to determine a possibility of precipitation.

13. The environmental alert system of claim 12 wherein:
the computing system is configured to determine a temperature value using the temperature reading and a humidity value using the humidity reading; and
the computing system is configured to determine the possibility of precipitation by plotting the temperature and humidity values against a saturation temperature curve.

14. The environmental alert system of claim 13, wherein the computing system is further configured to initiate an alert if the temperature and humidity values indicate a data point above the saturation temperature curve.

15. The environmental alert system of claim 10, wherein the first group of environmental sensors located on the insulative portion of the boom include both the humidity sensor and the moisture sensor.

16. An environmental alert system comprising:
at least one processor; and
one or more non-transitory computer readable storage media having a computer program stored thereon for alerting one or more users of an aerial device, wherein the computer program instructs the at least one processor to perform actions comprising:
initiating the program upon receiving an indication that a boom has been activated;
monitoring environmental conditions using a plurality of environmental sensors;
detecting values for one or more environmental conditions using the plurality of environmental sensors;
using the values to indicate a risk of reduced dielectric integrity of an insulating portion of a boom component; and
transmitting an alert to a user if the values indicate a risk of dielectric breakdown;
continually recording values received from the plurality of environmental sensors to identify trends indicative of a breakdown in dielectric integrity; and
initiating the alert upon a recognition of the breakdown in dielectric integrity.

17. The environmental alert system of claim 16, the actions further comprising:
   receiving temperature and humidity values and determining if the temperature and humidity values indicate a likelihood of precipitation; and
   executing the transmitting step if precipitation is determined to be likely.

18. An aerial device, comprising:
   a boom configured to be attached to a base and configured to extend upward and support a platform in a plurality of positions, said boom comprising a conductive portion and an insulative portion;
   one or more environmental sensors located on either the conductive portion of the boom or the insulative portion of the boom; and
   a computing system comprising at least one processor operatively connected to the one or more environmental sensors, the at least one processor configured to:
      receive a reading from the one or more environmental sensors and transmit an alert to a user of the aerial device, said alert indicating a detected environmental condition indicative of a breakdown in dielectric integrity of the insulative portion of the boom, and
      record values received from the one or more environmental sensors and transmit the alert based on a trend indicative of a breakdown in dielectric integrity of the insulative portion of the boom.

19. The aerial device of claim 18, wherein the one or more environmental sensors comprises at least two different sensors selected from the group consisting of a humidity sensor, a moisture sensor, and a temperature sensor.

20. The aerial device of claim 18, wherein the one or more environmental sensors includes at least two different kinds of sensors.

* * * * *